(12) United States Patent
Yoshimine

(10) Patent No.: US 7,546,204 B2
(45) Date of Patent: Jun. 9, 2009

(54) INFORMATION PROCESSOR, PORTABLE APPARATUS AND INFORMATION PROCESSING METHOD

(76) Inventor: Takashi Yoshimine, 5-3-107, Minami-cho, Toda-shi, Saitama, 335-0025 (JP)

( * ) Notice: Subject to any disclaimer, the term of this patent is extended or adjusted under 35 U.S.C. 154(b) by 541 days.

(21) Appl. No.: 10/565,726

(22) PCT Filed: May 12, 2004

(86) PCT No.: PCT/JP2004/006395
§ 371 (c)(1),
(2), (4) Date: Jan. 24, 2006

(87) PCT Pub. No.: WO2005/108926
PCT Pub. Date: Nov. 17, 2005

(65) Prior Publication Data
US 2006/0184318 A1    Aug. 17, 2006

(51) Int. Cl.
*G01C 21/26* (2006.01)
*G06F 19/00* (2006.01)
(52) U.S. Cl. .................... 701/209; 701/211; 701/213; 342/357.06
(58) Field of Classification Search .............. 701/209, 701/207, 211, 213, 300, 301; 340/348.1, 340/348.7, 686.6, 944; 342/357.06; 235/462.45
See application file for complete search history.

(56) References Cited
U.S. PATENT DOCUMENTS
4,712,003 A * 12/1987 Ban et al. .................. 250/221

5,807,111 A * 9/1998 Schrader .................... 434/112
6,011,754 A * 1/2000 Burgess et al. .............. 367/116
6,055,048 A * 4/2000 Langevin et al. ......... 356/237.1
6,542,811 B2 * 4/2003 Doi ............................ 701/200
7,308,314 B2 * 12/2007 Havey et al. ................. 607/54

FOREIGN PATENT DOCUMENTS

| JP | 08-202982 A | 8/1996 |
|---|---|---|
| JP | 2000-000262 A | 1/2000 |
| JP | 2000-205891 A | 7/2000 |
| JP | 2000-352925 A | 12/2000 |
| JP | 2001-086011 A | 3/2001 |
| JP | 2001-221649 A | 8/2001 |
| JP | 2001-318594 A | 11/2001 |
| JP | 2002-330807 A | 11/2002 |
| JP | 2003-070514 A | 3/2003 |
| JP | 2003-148967 A | 5/2003 |

OTHER PUBLICATIONS

International Search Report mailed on Aug. 17, 2004.

* cited by examiner

*Primary Examiner*—Tan Q Nguyen
(74) *Attorney, Agent, or Firm*—Rader, Fishman & Grauer, PLLC

(57) ABSTRACT

An object of the present invention is to provide a technology that improves the safety of a handicapped person when he or she goes out. In addition, another object of the present invention is to provide a technology that generates route information or surrounding information that a handicapped person can easily understand.

A mount device 20 mounted to the head of a handicapped user 5 acquires information in the eye level of the user. A portable device 30 that the user 5 holds with his or her hand acquires information in the forward foot level of the user. Thus, since more detailed information can be acquired, the safety of the user 5 who goes out is improved.

11 Claims, 13 Drawing Sheets

| VIBRATION BUTTON | INSTRUCTION | VIBRATION PATTERN |
|---|---|---|
| 303 | RIGHT TURN |  |
| 304 | LEFT TURN |  |
| 305 | GO STRAIGHT |  |
| 306 | PRESENCE OF OBSTACLE |  |
| 307 | OTHER |  |

INFORMATION PROCESSOR, PORTABLE APPARATUS AND INFORMATION PROCESSING METHOD

FIELD OF THE INVENTION

The present invention relates to an information processing apparatus, a portable device, and an information processing method that support going-out of visually handicapped people.

BACKGROUND OF THE INVENTION

So far, many technologies that support going-out of visually handicapped people have been proposed. Examples of these technologies are cameras that capture surrounding environments of users who are walking and sticks having sensors that detect obstacles in front of the users (see paragraph [0225], FIG. 15, Japanese Patent Laid-Open Publication No. 2003-70514). In the stick as the related art, as means that informs the user of the surrounding situation, a vibrator that vibrates according to an output signal of a sensor is used.

DISCLOSURE OF THE INVENTION

Problems to be Solved

Beside that, a system that detects a user's position using the global positioning system (GPS) has been proposed (see for example paragraph [0013], FIG. 1, Japanese Patent Laid-Open Publication No. 2001-221649, paragraph [0011], FIG. 1, Japanese Patent Laid-Open Publication No. 2000-262, and paragraph [0037], FIG. 1, Japanese Patent Laid-Open Publication No. 2000-205891.

The technologies disclosed in those patent documents acquire picture information of the user with a camera. It seems that the user needs more detailed picture information.

With the technology of Patent Document 1, the user needs to memorize the vibration patterns of the vibrator. If the user does not memorize or forget them or misunderstands them, he or she may face very dangerous situations.

From the foregoing point of view, an object of the present invention is to provide a technology that improves the safety of a handicapped person when he or she goes out.

Another object of the present invention is to provide a technology that generates route information or surrounding information that a handicapped person can easily understand.

Means for Solving the Problem

The present invention is an information processing apparatus, comprising, a mount device that is capable of being mounted to the user's head and that is capable of acquiring first picture information from information of user's surroundings, and a portable device having means for storing map information, means for acquiring user's any position information and second picture information of the user's surroundings, the second picture information being different from the first picture information, means for setting a user's destination, means for searching the map information for the destination that has been set and setting a route to the destination according to user's present position information, and first informing means for informing the user of at least route information that has been set of the route information, the user's first picture information on the route and the user's second picture information on the route with vibration.

According to the present invention, the information of the user's surrounding information is information about obstacles at his or her feet and over his or her head, traffic information in a predetermined range around the user, or information about stores and facilities. The head is a portion higher than the user's neck. Thus, the head may be the user's face or user's parietal portion. The first picture information is for example picture information around the user's head and picture information in the user's eye level. The portable device is a device that the user can hold with his or her hand. The second picture information is for example picture information at the user's feet. The user's feet represent a range around from 50 cm to 3 m in front of the user and a range around from 0 cm to 50 cm above the ground level.

According to the present invention, since the first picture information is acquired from the mount device mounted to the user's head and the second picture information is acquired from the portable device that the user holds with his or her hand, more detailed information can be acquired. Thus, the safety of the user is improved when he or she goes out.

Specifically, the first informing means has means for converting the route information that has been set, the first picture information, and the second picture information into a predetermined signal pattern and a vibration button that vibrates according to the converted signal pattern.

According to an aspect of the present invention, the mount device has second informing means for informing the user of at least one of the route information, the first picture information, and the second picture information with sound. When the user is informed of each information with vibration and sound, he or she can easily understand each information. Thus, the safety of the user is more improved.

According to an aspect of the present invention, the portable device also has a sensor that detects an obstacle. The first informing means or the second informing means has means for informing the user of information of the obstacle according to a detection signal of the sensor. Thus, since an obstacle can be easily detected, the safety of the user is improved. The sensor that detects an obstacle is for example an ultrasonic sensor, an infrared sensor, or the like. With the sensor, the distance to the obstacle can be detected.

According to an aspect of the present invention, the portable device has a first surface and a second surface opposite to the first surface. The first informing means has a plurality of vibration buttons that vibrate user's fingers. The vibration buttons are composed of a first vibration button and a second vibration button disposed on the first surface and the second surface, respectively. Thus, since the positions of the vibration buttons fit the arrangements of the user's hand and fingers, he or she can easily sense the vibration.

According to an aspect of the present invention, the first informing means has means for informing the user of a right-turn instruction and a left-turn instruction as the route information through the first vibration button and the second vibration button, respectively. Since the user can intuitionally know the route information, the load of the user for example he or she needs to memorize the vibration patterns can be decreased as much as possible. In addition, the safety of the user improves. In this case, the portable device (excluding the vibration buttons) needs to be asymmetrical with respect to for example a predetermined axis or surface. In other words, if the portable device is symmetrical with respect to for example the center surface between the first surface and the second surface, when the user holds the portable device with his or her hand, he or she cannot know which vibration keys are the first vibration key and the second vibration key. However, when the portable device is asymmetrical with respect to for example a predetermined axis or surface, such inconvenience can be solved. Specifically, a mark such as unevenness may be formed on the portable device.

According to an aspect of the present invention, the first informing means is means for informing the user of the first picture information and the second picture information through the first vibration button and the second vibration button, respectively. Thus, the user can intuitively know whether picture information is acquired by the mount device or the portable device. In addition, the load of the user for example he or she needs to memorize the vibration patterns can be decreased as much as possible. Moreover, the safety of the user improves.

According to an aspect of the present invention, the portable device has a first surface, a second surface opposite to the first surface, and a third surface nearly perpendicular to the first surface and the second surface. The first informing means has a plurality of vibration buttons that vibrate user's fingers. Each of the vibration buttons is composed of a first vibration button, a second vibration button, and a third vibration button disposed on the first surface, the second surface, and the third surface, respectively. Thus, since the positions of the vibration buttons fit the arrangements of the user's hand and fingers, he or she can easily sense the vibration.

According to an aspect of the present invention, the first informing means informs the user of a right-turn instruction, a left-turn instruction, and a go-straight instruction as the route information through the first vibration button, the second vibration button, and the third vibration button, respectively. Thus, since the user can intuitively know the route information, the load of the user for example he or she needs to memorize the vibration patterns can be decreased as much as possible. In addition, the safety of the user improves.

According to an aspect of the present invention, the portable device has an upper surface portion and a lower surface portion. The upper surface portion has a first forward portion and a first backward portion. The lower surface portion has a second forward portion and a second backward portion. The lower surface portion is opposite to the upper surface portion. The first informing means has a plurality of vibration buttons that vibrate user's fingers. The vibration buttons are composed of a first vibration button, a second vibration button, a third vibration button, and a fourth vibration button disposed on the first forward portion, the first backward portion, the second forward portion, and the second backward portion, respectively. The "forward" of the forward portion represents the direction of the destination of the user on the route. Instead, the "forward" may be the direction in which the user walks. The "backward" of the backward portion represents the reverse direction of the forward direction. In this structure, the user can intuitively know information about forward, backward, leftward, and rightward. In particular, it is preferred that the third vibration button be composed of a left vibration button and a right vibration button disposed leftward and rightward, respectively.

According to an aspect of the present invention, the first informing means has means for varying the state of the vibration according to at least one of the route information, the first picture information, and the second picture information. Thus, the user can obtain more detailed information. The case that the vibration varies according to route information is for example when the information processing apparatus outputs a right-turn instruction, the vibration becomes stronger as the user gets closer to the right turn position.

According to an aspect of the present invention, the first informing means has a plurality of vibration buttons that vibrate the user's fingers and means for outputting information in combination of vibration states of the vibration buttons. Thus, the user can obtain more detailed information.

According to an aspect of the present invention, the portable device also has means for storing position information of a predetermined facility as the map information and means for informing the facility of the user's physiological state according to a user's operation input. The route setting means has means for setting a route from the user's present position to the informed facility according to a user's operation input signal. Thus, the safety of the user can be secured. The physiological state is for example the state that the user wants to go to the bathroom. The physiological state also includes a condition of the user such as sickness.

According to an aspect of the present invention, the mount device has an identifier that is disposed on the exterior of the mount device and that identifies a handicapped person. Thus, a person who is near the user can quickly recognize him or her as a handicapped person.

According to an aspect of the present invention, solar power generation means is disposed in at least one of the mount device and the portable device. In particular, if the battery of the information processing apparatus runs out, the user faces a critical situation. Thus, the self-power generation is essential.

Instead of the solar power generation means, mechanical power generation means may be used. Since the user puts on or holds the information processing apparatus with his hand while he or she is walking, the information processing apparatus moves. Thus, the power generation means using dynamic energy is effective.

The present invention is a portable device, comprising means for storing map information, means for acquiring user's any position information and second picture information different from first picture information acquired by a mount device from information of user's surroundings, the mount device being capable of being mounted to the user's head, means for setting a user's destination, means for searching the map information for the destination that has been set and setting a route to the destination according to the user's present position information, and means for informing the user of at least route information that has been set of the route information, the user's first picture information on the route and the user's second picture information on the route with vibration.

The present invention is an information processing method, comprising the steps of storing map information, causing a mount device capable of being mounted to the user's head to acquire first picture information from information of user's surroundings, acquiring user's present position information as map information, setting a user's destination, searching the map information for the destination that has been set, setting a route to the destination according to the user's present position information, causing a portable device that the user is capable of carrying to acquire second picture information from the information of the user's surroundings, the second picture information being different from the first picture information, and informing the user of at least route information that has been set of the route information, the first picture information on the route and the second picture information on the route with vibration of the first vibration button and the second vibration button of the portable device.

EFFECTS OF THE INVENTION

Thus, according to the present invention, the safety of a handicapped person is improved when he or she goes out. In addition, route information or surrounding information that a handicapped person can easily understand can be generated.

BEST MODE FOR CARRYING OUT THE INVENTION

Next, with reference to the accompanying drawings, embodiments of the present invention will be described.

FIG. 1 is a block diagram showing the structure of an information processing apparatus according to an embodiment of the present invention. The information processing apparatus is denoted by reference numeral 1. The information processing apparatus 1 is composed of a face mount device (hereinafter referred to as the mount device) 20 that a user 5 who is a visually handicapped person can put on his or her face and a portable device 30 that the user 5 can hold with his or her hand.

The mount device 20 has a CPU 21, a read-only memory (ROM) 22, a random access memory (RAM) 23, a speaker 24, a plurality of cameras 25, a microphone 26, and a communication section 27. The CPU 21 controls the whole mount device 20. The ROM 22 stores predetermined software and so forth. The RAM 23 is a work area of the CPU 21.

FIG. 2 shows the state that the user 5 puts on the mount device 20. The speaker 24 gives sound instructions to the user 5 who is walking so that he or she can arrive at his or her destination. The cameras 25 capture picture information of the surroundings of the user 5. In particular, the cameras 25 capture picture information of the surroundings of the head of the user 5 or picture information in the eye level of the user 5. The cameras 25 are of for example a charge coupled device (CCD) or a complementary metal-oxide semiconductor (CMOS) sensor type. A lens system focuses an image on the CCD or COMS sensor.

The microphone 26 converts voice of the user 5 into for example an electric signal. The communication section 27 is a mechanism that wirelessly or non-wirelessly communicates with the portable device 30. In particular, when the mount device 20 communicates with the portable device 30 through a cable, even if the user 5 lefts the portable device 30 from his or her hand, the portable device 30 does not drop to the ground. Thus, there is no inconvenience since the user 5 does need to look for the portable device 30 that dropped to the ground.

FIG. 5 is a schematic diagram showing software stored in the ROM 22. The software is for example a picture recognition program 51 that recognizes pictures captured by the cameras 25 and an audio process program 52 that gives the user 5 audio information processed according to the information processed by the picture recognition program 51 through the speaker 24. The audio process program 52 also recognizes voice of the user 5 through the microphone 26. As will be described later, the portable device 30, not the audio process program 52, generates audio data for a route guide to the destination.

As shown in FIG. 1, the portable device 30 is a device that guides the walking of the user 5. The portable device 30 has a CPU 31, a read-only memory (ROM) 32, a random-access memory (RAM) 33, a database section 36, a GPS radio wave reception section 34, a communication section 35, a camera 37, a vibration section 38, and an ultrasonic sensor 39.

The CPU 31 controls the whole portable device 30. The ROM 32 stores predetermined software and so forth. The RAM 23 is a work area of the CPU 21. As shown in FIG. 6, the ROM 32 stores a navigation program 40, a picture recognition program 45, and an audio process program 46. The navigation program 40 has a route search function 41, a destination set/change function 42, a present position acquisition function 43, and so forth. The picture recognition program 45 recognizes a pictures captured by the camera 37. The audio process program 46 generates audio guide data that guides the user to the destination and audio data that informs the user 5 of information processed according to the picture recognition program 45.

The database portion 36 is composed of a hard disk device, a flash memory, or the like in which data can be rewritten. The database portion 36 stores for example map data 11, facility registration data 12, vibration pattern data 13, and so forth. The facility registration data 12 are registered data of facilities such as convenience stores, supermarkets, department stores, schools, hospitals, restaurants, stations, companies, and so forth. They are registered with their names or the like. Position data of these facilities are registered as coordinates on the map data 11.

The GPS radio wave reception section 34 receives radio waves from satellites 6. For example, five to ten satellites 6 are used. At present, the positioning accuracy of the GPS is as high as 30 cm. In future, it is expected that the positioning accuracy of the GUP will be as high as 1 cm. The communication section 35 communicates with the mount device 20 and an external device such as a cellular phone as will be described later. The vibration section 38 vibrates to inform the user 5 of information of the surroundings while he or she is walking.

FIG. 3 is a perspective view showing the portable device 30. FIG. 4 is a schematic diagram showing the state that the user 5 is holding the portable device 30 with his or her hand.

A main body 301 is provided with an antenna 302 that composes a part of the GPS radio wave reception section 34. Disposed on a first side surface 301a of the main body 301 are a vibration button 303 and on a second side surface 302a opposite to the first side surface 301a are vibration buttons 304, 305, 306, and 307. These vibration buttons 303 to 307 compose a part of the vibration section 38. As shown in FIG. 4, the vibration button 303 is used for the thumb. The vibration buttons 304 to 307 are used for the index finger, middle finger, ring finger, and little finger.

Disposed at a lower portion of the main body 301 are the camera 37, whose angle can be freely changed in for example the arrow direction, and the ultrasonic sensor 39. Like the cameras 25 of the mount device 20, the camera 37 can be composed of a CCD sensor or a CMOS sensor. When the user 5 holds the portable device 30 with his or her hand, the camera 37 can capture a picture of a region different from pictures that the cameras 25 of the mount device 20 capture. The ultrasonic sensor 39 detects an obstruct with a sound reflected therefrom.

FIG. 7 is a block diagram showing the structure of the vibration section 38 shown in FIG. 1. The vibration buttons 303 to 307 are driven by vibration motors M1 to M5, respectively. The vibration motors M1 to M5 each have for example an eccentric weight. The vibration patterns of the vibration motors M1 to M5 are controlled by a vibration controller 310. The vibration patterns are for example strength and weakness of vibration, high and low frequencies of vibration, or the like. The vibration controller 310 controls the vibrations of the vibration motors M1 to M5 according to the guide information of the navigation program 40. Instead, the vibration controller 310 may vibrate the vibration motors M1 to M5 in synchronization with timing at which audio data generated according to the audio process programs 52 and 46 are output from the speaker 24.

FIG. 8 is a schematic diagram showing an example of vibration pattern data stored in the database section 36. When the instruction given to the user 5 is for example "right turn," the vibration controller 310 vibrates the thumb vibration button 303 so that the user 5 is informed of the instruction at constant time intervals of t1. The time interval t1 is for example in the range from 1 second to several seconds. t2 is a duration for which the vibration button 303 vibrates. The vibration button 303 vibrates for the duration t2 a predetermined number of times. The more the user 5 approaches the right turn point, the larger the amplitude of the vibration becomes.

Next, the operation of the information processing apparatus 1 will be described. FIG. 9 describes the operation of the information processing apparatus 1 with an example of map information indicating a route from the present position of the user 5 to the destination. In FIG. 9, it is assumed that the user 5 will go to a destination, facility A. In addition, it is assumed that the user 5 knows what facility A is. In FIG. 9, reference numerals 19a to 19d represent traffic signals.

First, the portable device 30 acquires the present position of the user 5. Specifically, with the navigation program 40, the CPU 31 calculates the present position on the map data 11 according to radio waves received by the GPS radio wave reception section 34 and acquires the present position of the user 5.

When the user 5 has obtained the present position, he or she sets the mount device 20 for the destination, facility A, through the microphone 26 of the mount device 20. For example, the user 5 can set the mount device 20 for the destination, facility A, by pronouncing the name of facility A. Specifically, the CPU 21 recognizes the voice of the user 5 that is input through the microphone 26 according to the audio process program 52, converts the voice into an electric signal, and transmits the electric signal to the portable device 30 through the communication section 27. When the portable device 30 receives the signal through the communication section 35, the CPU 31 references the map data 11 and the facility registration data 12 and sets the portable device 30 for the destination, facility A.

When the portable device 30 has been set for the destination, facility A, as shown in FIG. 10, the user 5 starts walking with the portable device 30 so that it faces forward. As shown in FIG. 4, the user 5 holds the portable device 30 with his or her hand so that the portable device 30 faces forward. With the posture of the user 5, the cameras 25 of the mount device 20 capture information in the eye level (picture capturing range 60) of the user 5. The camera 37 of the portable device 30 captures information in the forward foot level of the user 5 (picture capturing range 70) (see FIG. 4).

When the portable device 30 has been set for the destination, facility A, the vibration controller 310 vibrates the "straight" vibration button 306 to instruct the user 5 to go straight. Thereafter, the CPU 21 of the mount device 20 causes the cameras 25 to monitor the front of the user 5. When there is an obstruct, the CPU 21 causes the speaker 24 to inform the user 5 of an instruction such as "there is a utility pole," "there is a bicycle," "a bicycle is coming," or the like according to the audio process program 52. On the other hand, the CPU 31 of the portable device 30 causes the camera 37 and the ultrasonic sensor 39 to monitor an obstacle in the foot level of the user 5 and sends the acquired information to the mount device 20 through the communication section 35. The CPU 21 of the mount device 20 causes the speaker 25 to inform the user 5 of an instruction such as "there is a step," "the walkway will soon end," or the like according to the audio process program 52. If there is an obstacle, the CPU 21 may cause the vibration button 307 to inform the user 5 of it with vibration along with sound. Since the portable device 30 uses not only the ultrasonic sensor 39 but the camera 37, the portable device 30 can inform the user 5 of more accurate information and thereby improve the safety of the user 5.

Information acquired by the mount device 20 may be inconsistent with information acquired by the portable device 30. In this case, when the mount device 20 has a buffer such as a first-in first-out (FIFO) or the like, a controller that controls the data amount and data output timing of the FIFO, and so forth, the inconsistence can be prevented. As a result, the safety of the user 5 is improved.

When the user 5 is approaching a left turn point 15, the vibration controllers 310 causes the vibration button 304 to start vibrating. For example, within 30 to 10 meters of the left turn point 15, the vibration controller 310 causes the vibration button 304 to start vibrating. At this point, when the vibration controller 310 causes the vibration button 304 more strongly to vibrate as the user 5 more approaches the left turn point 15, he or she can intuitionally know the left turn point 15. At this point, when the CPU 31 causes the "go straight" vibration button 306 more weakly to vibrate as the user 5 more approaches the left turn point 15, he or she can more intuitionally know the left turn point 15.

When the user 5 has tuned left at the left turn point 15, the vibration controller 310 causes the "go straight" vibration button 306 to vibrate again to instruct the user 5 to "go straight." When the user 5 approaches an intersection 16, the cameras 25 capture a traffic signal 19a or the like and the CPU 21 instructs the user 5 to "go straight" or "stop." Instead, the CPU 21 may inform the user 5 that "The traffic signal is blue." or "The traffic signal is red." At this point, as the user 5 is more approaching the intersection 16, the CPU 31 causes the "straight" vibration button 306 more weakly to vibrate.

When the user 5 has crossed the intersection 16, the vibration controller 310 instructs the user 5 to "go straight." As the user 5 more approaches a right turn point 17, the vibration controller 310 causes the "right turn" vibration button 303 more strongly to vibrate. When the user 5 has turned right, he or she walks straight and approaches a diagonal left turn point 18. As the vibration controller 310 more approaches the left turn point 18, the vibration controller 310 causes the "left turn" vibration button more strongly to vibrate. For safety, the CPU 21 may cause the speaker 24 to instruct the user 5 to for example "Diagonally turn left."

When the user 5 is approaching facility A, the CPU 21 causes the speaker 24 to inform the user 5 that "We have more . . . meters to the destination." When the user 5 has arrived at facility A, the CPU 21 causes the speaker 25 to inform the user 5 that "We have arrived the destination."

As described above, according to the embodiment of the present invention, the mount device 20 that the user 5 can put on his or her head can acquire information in the forward eye level of the user 5. In addition, the portable device 30 that the user 5 holds with his or her hand can acquire information in the forward foot level of the user 5. Thus, since the user can obtain more detailed information from both the mount device 20 and the portable device 30, the safety of the user 5 is improved when he or she goes out.

According to the embodiment of the present invention, as shown in FIG. 3 and FIG. 4, disposed on the first side surface 301a of the portable device 30 are the vibration button 303 and on the side surface 302a opposite to the first side surface 301a are the vibration buttons 304, 305, 306, and 307. Thus, since the vibration buttons fit the hands and fingers of the user 5, he or she can easily feel the vibrations.

According to the embodiment of the present invention, since the vibration buttons 303 and the vibration button 304 are designated to instruction "right turn" and instruction "left turn," respectively. Thus, the user 5 can intuitively know information of the route. Thus, the load of the user who needs to memorize vibration patterns can be decreased as much as possible. In addition, the safety of the user is improved.

According to the embodiment of the present invention, with the ultrasonic sensor 39, the distance from the user to an obstacle can be acquired. When the user 5 is informed of this distance with the speaker 24 of the mount device 20, the safety of the user 5 is more improved. Instead, without the ultrasonic sensor 39, the distance from the user 5 to an obstacle can be acquired by the two cameras 25 of the mount device 20 according to the picture analysis software.

FIG. 11 is a perspective view showing a portable device according to another embodiment of the present invention. In this embodiment, description of similar sections, functions, and so forth of the portable device of the embodiment to those of the portable device 30 of the foregoing embodiment will be simplified or omitted. Only different points will be described. This applies to other embodiments shown in FIG. 12 to FIG. 15.

The portable device is denoted by reference numeral 80. Disposed on a third side surface 801c of a main body 801 of the portable device 80 is a vibration button 804 for the index finger. In this case, a vibration button 803, a vibration button 805, and a vibration button 804 are designated to "right turn," "left turn," and "go straight," respectively. Thus, the user 5 can more intuitively know these vibration buttons.

At least one of the vibration buttons 803 to 807 may be disposed on a fourth side surface 801d. The third side surface 801c (fourth side surface 801d) is nearly perpendicular to the first side surface 801a and the second side surface 801b.

FIG. 12 and FIG. 13 are a perspective view and a plan view showing a portable device according to a further other embodiment of the present invention.

The portable device according to this embodiment is denoted by reference numeral 90. The portable device 90 has a main body section 901 and a protrusion section 902. The user 5 holds the portable device 90 with his or her hand. The user 5 can hold the main body section 901 by stretching his or her index finger 72 around the main body section 901. In FIG. 12 and FIG. 13, Y direction represents that direction in which the user 5 walks, whereas X direction represents the left and right directions of the user 5. Disposed at a front portion of an upper surface 901a of the main body section 901 is a vibration button 903 for a thumb 71. Disposed on a lower surface 902b of the protrusion section 902 are vibration buttons 904 and 905 for an index finger 72. Disposed at a rear portion of an upper surface 901a of the main body section 901 are vibration buttons 906, 907, and 908 for a middle finger 73, a ring finger 74, and a small finger 75, respectively. Disposed at a rear portion of a lower surface 901b of the main body section 901 are vibration buttons 909, 910, and 911 for the middle finger 73, the ring finger 74, and the small finger 75, respectively.

For example, the vibration button 903, the vibration button 904, and the vibration button 905 may be assigned to "go straight," "right turn," and "left turn," respectively. In addition, the vibration buttons 906, 907, and 908 on the upper surface 901a may be assigned to information acquired by the mount device 20. On the other hand, the vibration buttons 909, 910, and 911 on the lower surface 901b may be assigned to information acquired by the portable device 90.

With the structure of the portable device 90, the user 5 can intuitively know information of the route and information of the surroundings. Thus, the load of the user 5 who needs to memorize vibration patterns can be decreased. In addition, the safety of the user 5 is improved. Moreover, the user 5 does not need to raise the portable device 90 with his or her hand.

Instead, the user 5 can walk with hanging the portable device with his or her hand. Thus, the load of the user 5 can be decreased when he or she walks.

According to this embodiment, a camera may be disposed on the front surface 901c or the lower surface 901b of the main body section 901.

FIG. 14 is a front view showing a mount device according to another embodiment of the present invention. The mount device is denoted by reference numeral 50. Disposed between two cameras 25 of the mount device 50 is a solar panel 7. The solar panel 7 converts light energy into electric energy. With the electric energy, the mount device 50 is operated. Of course, it is preferred that the mount device 50 be energized with both the solar panel and another battery cell. The portable device may be also provided with such solar power generation means.

In addition, an identifier that identifies the user as a visually handicapped person may be disposed outside the mount device. For example, as shown in FIG. 14, the color of an antenna 88 may be standardized for a visually handicapped person. The visually handicapped person may be identified by characters or graphics as well as a color. Such an identifier may be added to the portable device.

FIG. 15 is a partial sectional view showing a portable device according to a further other embodiment of the present invention. The portable device is denoted by reference numeral 100. Disposed in a main body 301 of the portable device 100 is a mechanical power generation section 333. The power generation section 333 has a coil 311, an iron core 312, and a pair of spring members 314. The spring members 314 are disposed at both ends of the iron core 312 around which the coil 311 is wound. Thus, when the user 5 walks with the portable device 100, elastic force of the spring members 314 generates electric power. The mount device may be provided with such mechanical power generation means.

The present invention is not limited to the foregoing embodiments. Instead, the present invention may be modified in various manners.

The portable device may have an emergency button. When the user 5 wants to go to the bathroom, he or she may press the emergency button. As a result, the portable device may transmit an emergency signal to a nearby facility such as a convenience store through the communication section 35. In this case, the portable device may search the database section 36 for the facility, set the destination for the facility, and guide the user 5 to the facility. When a nearby facility receives the emergency signal, the facility may open the bathroom to the user 5 and perform a proper preparation for him or her. Specifically, an employee of the facility may receive the user 5 at the entrance. This applied to the case that the user 5 gets sick suddenly. This structure allows the safety of the body of the user 5 to be secured. A signal that the portable device transmits may be managed by for example a management center and transferred to each facility therethrough.

In the foregoing embodiments, as the obstacle sensor, the ultrasonic sensor 39 was used. Instead, a laser or the like may be used. Instead, as the obstacle sensor, an infrared sensor may be used.

The portable device 30 shown in FIG. 3 and FIG. 4 is used for the user 5 who is right-handed. Of course, a portable device for the user 5 who is left-handed may be used. This portable device is symmetrical to the portable device 30.

In addition, the vibration patterns of the vibration buttons of the portable device may be customized so that the user 5 can easily memorize them.

In addition, map information may be downloaded from a center. In this case, map information may be automatically updated at intervals of a predetermined period. Map information to be downloaded may be only map data shown in FIG. 6, only facility registration data, or both of them.

In FIG. 9, it was assumed that the user 5 knows what facility A is. Instead, when the user 5 wants to go to a hospital, if he or she does not know where it is or its name, by pronouncing "hospital," the portable device may search the map data 11 for a nearby hospital and sets the destination for it.

EXPLANATION OF CODES

Figure 1:
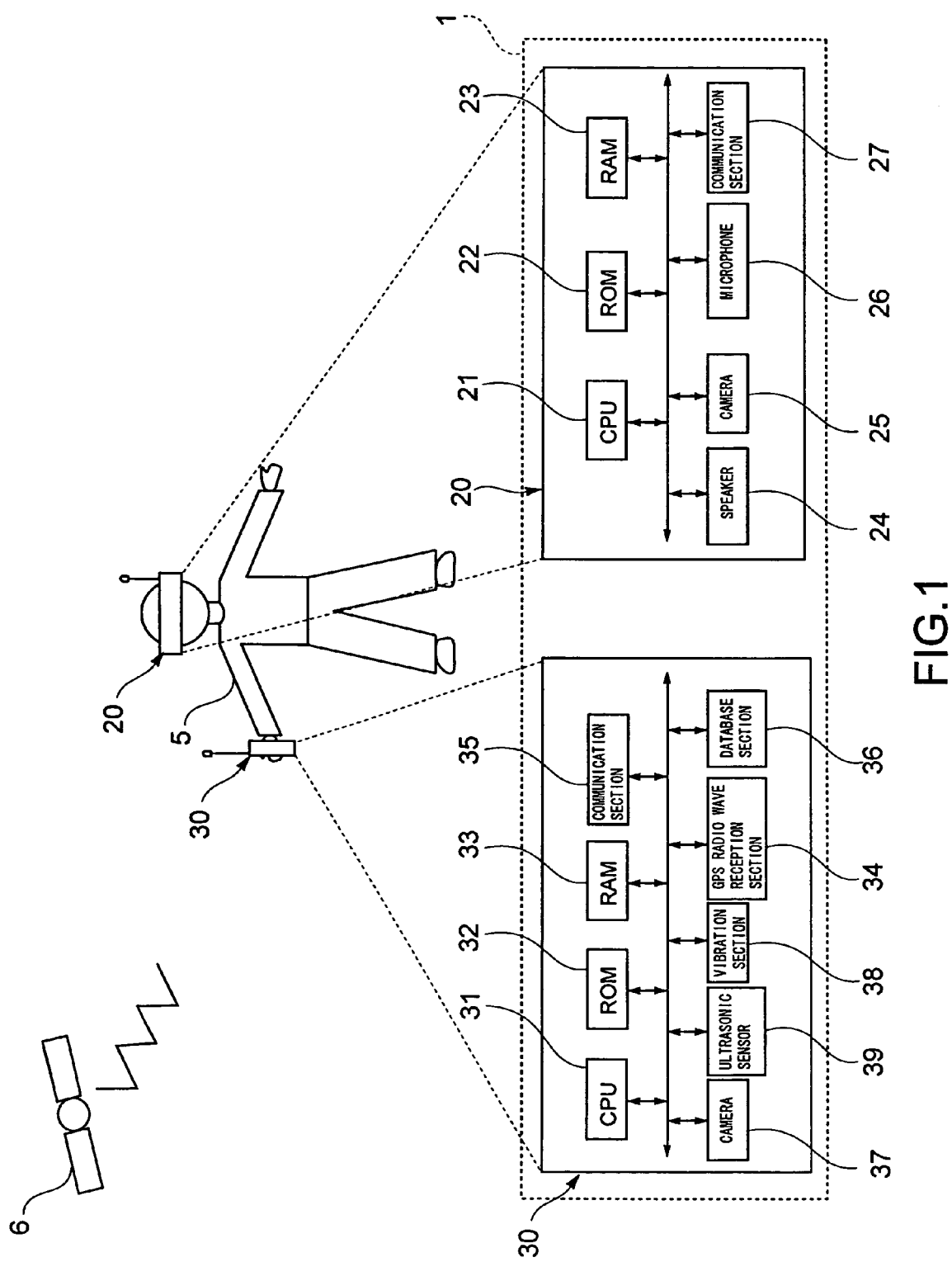
FIG. 1 is a block diagram showing the structure of an information processing apparatus according to an embodiment of the present invention.
Figure 2:
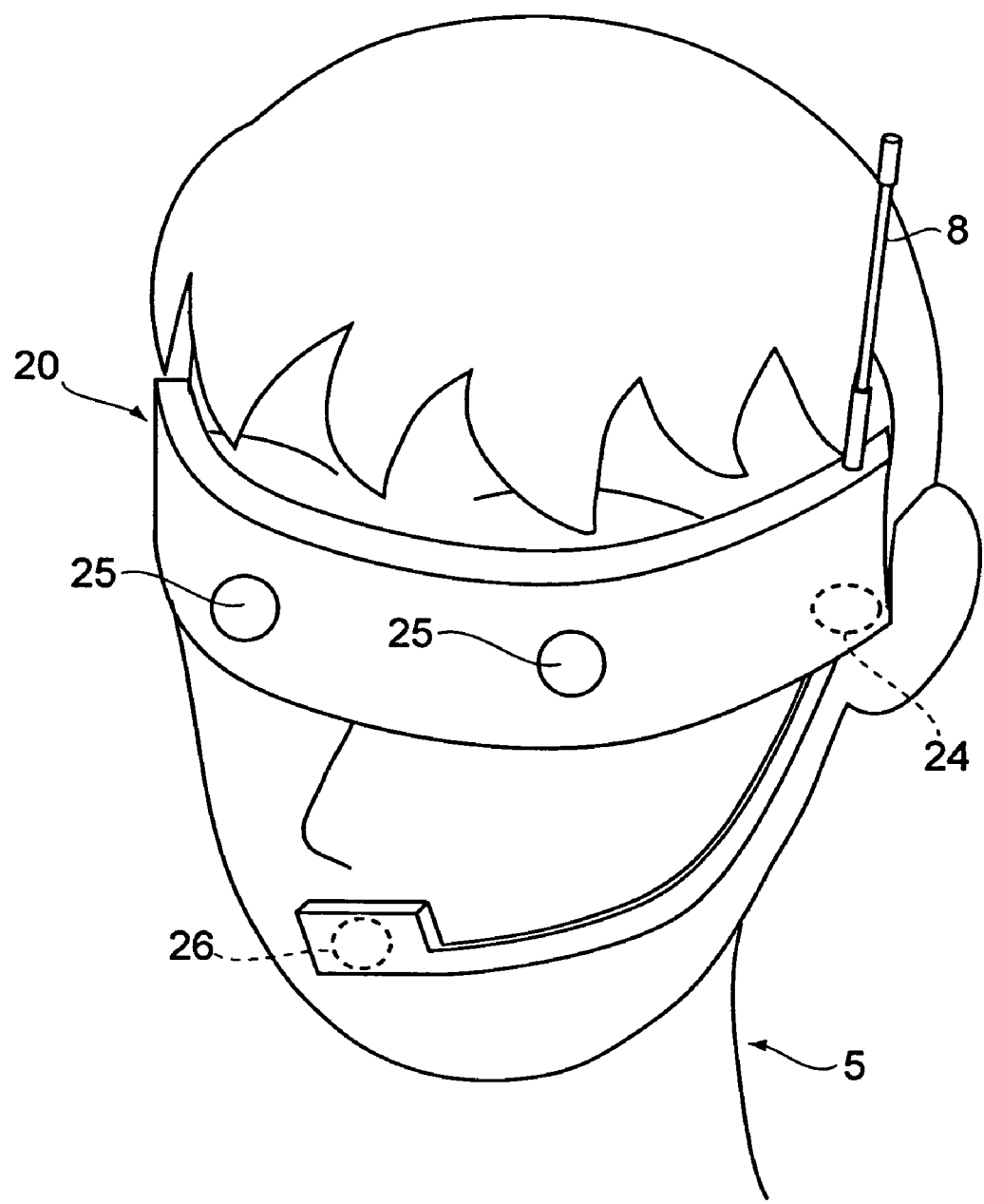
FIG. 2 is a block diagram showing the state that the user puts on a mount device.
Figure 3:
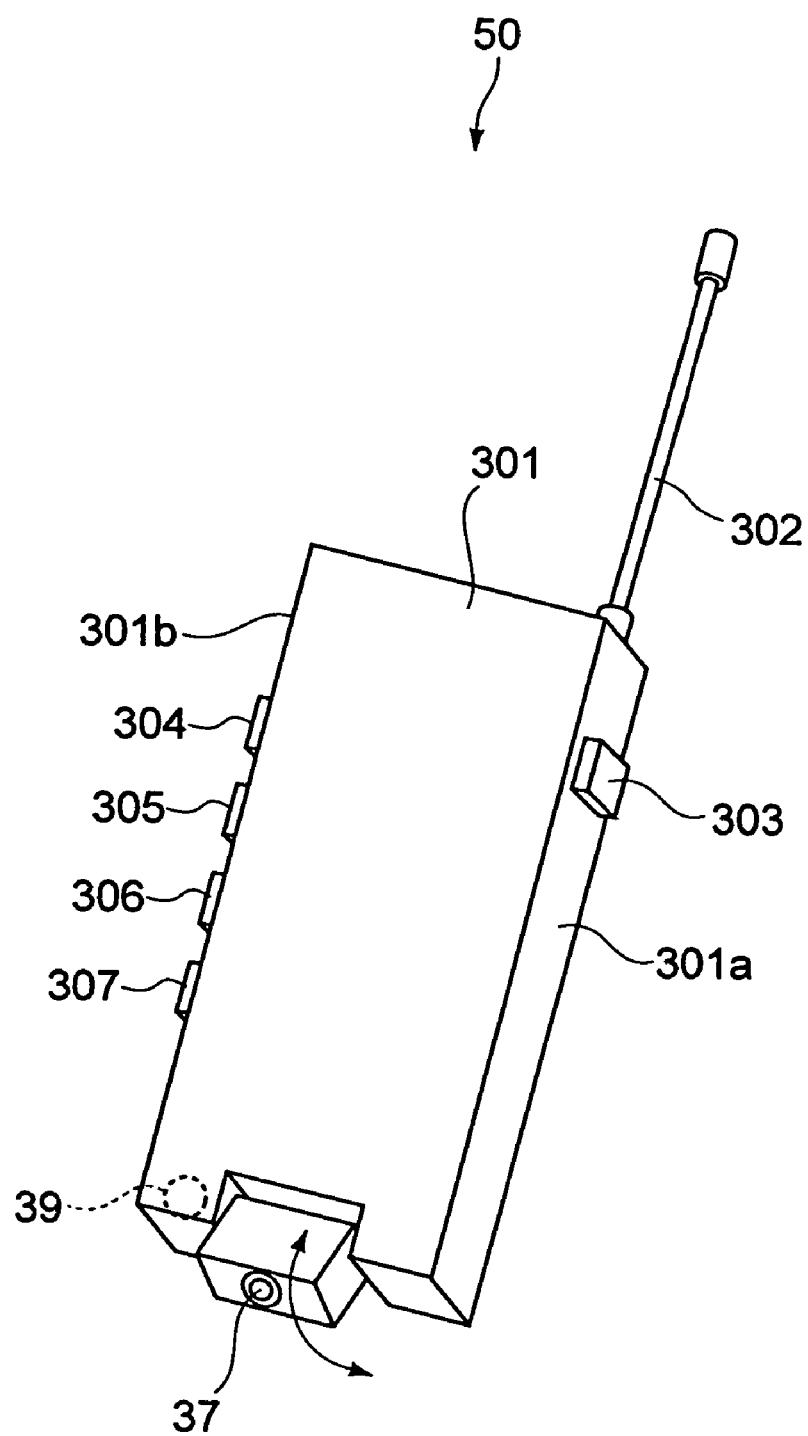
FIG. 3 is a perspective view showing a portable device.
Figure 4:
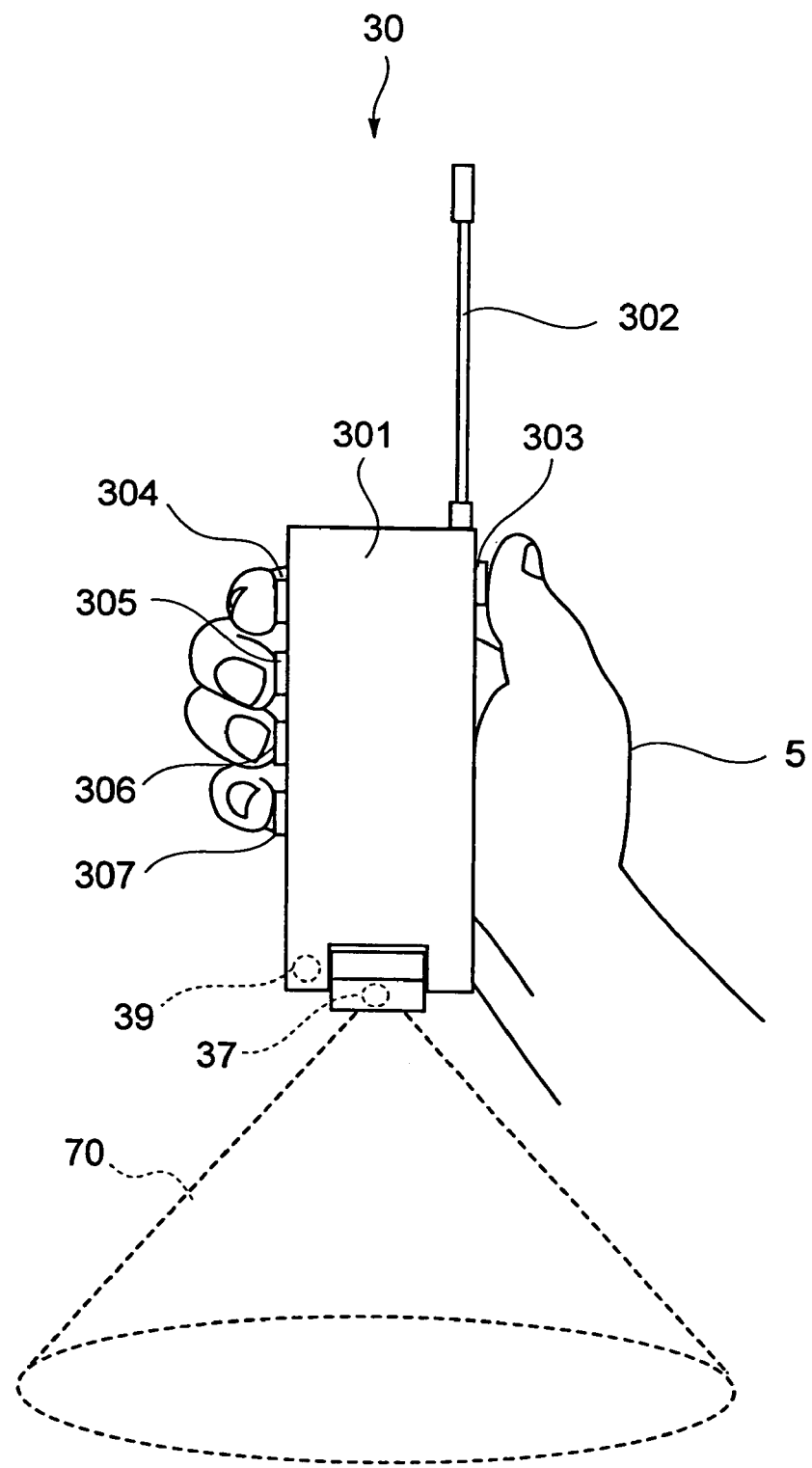
FIG. 4 is a schematic diagram showing the state that the user holds the portable device with his or her hand.
Figure 5:
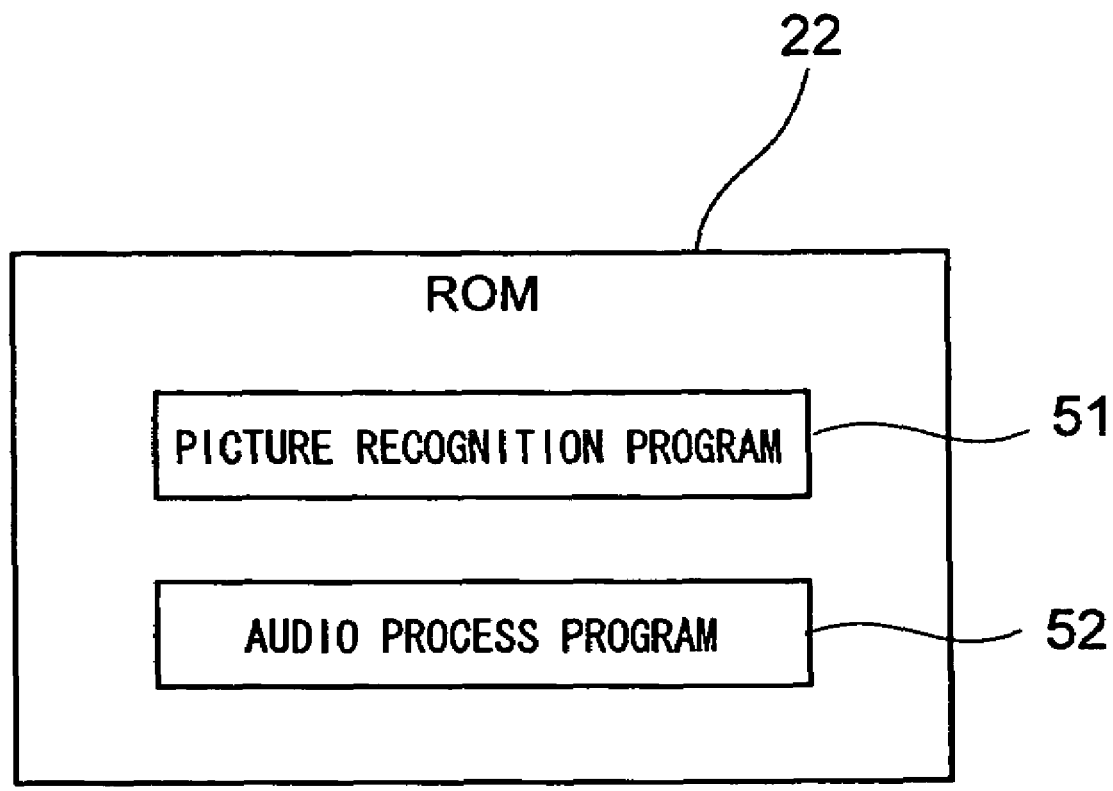
FIG. 5 is a schematic diagram showing software stored in a ROM of the mount device.
Figure 6:
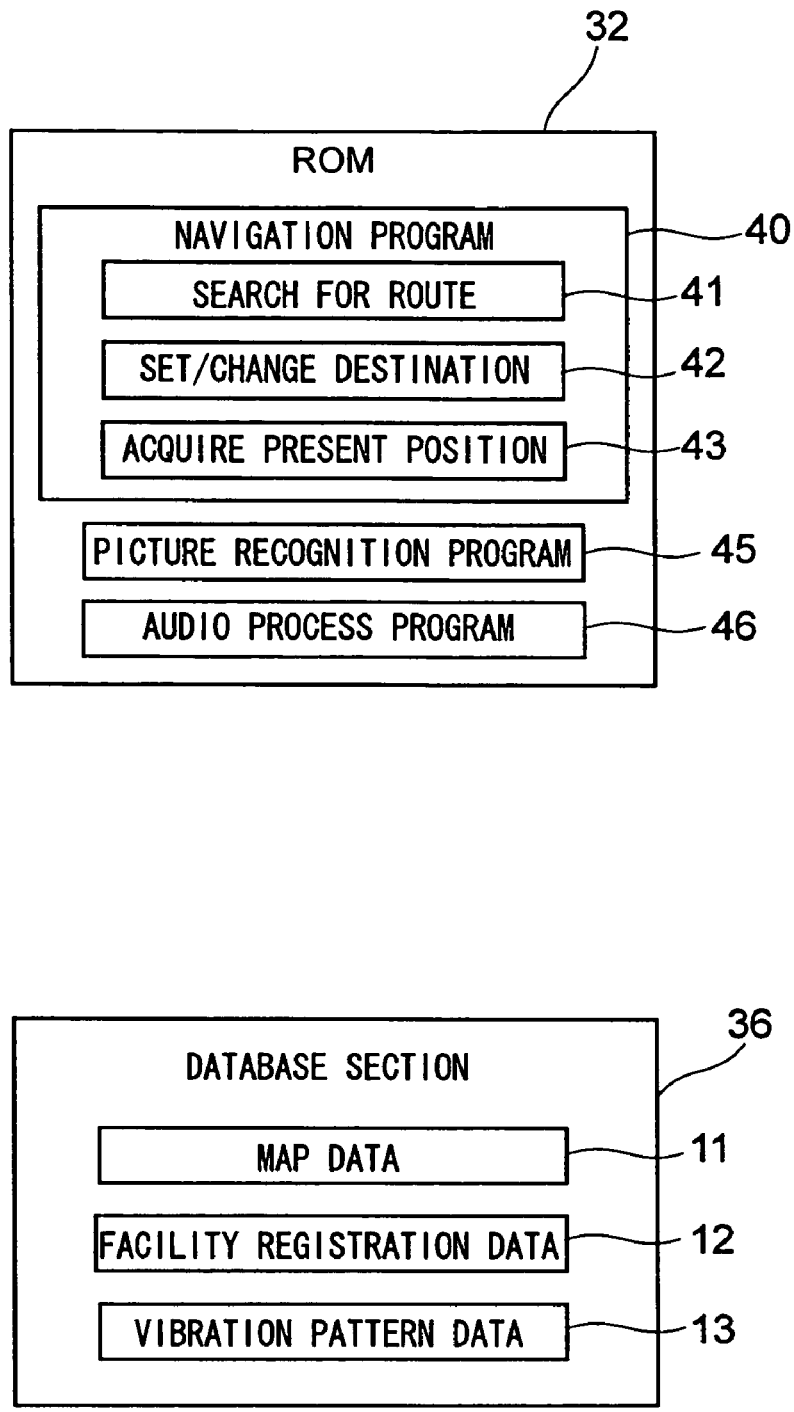
FIG. 6 is a schematic diagram showing software stored in a ROM of the portable device.
Figure 7:
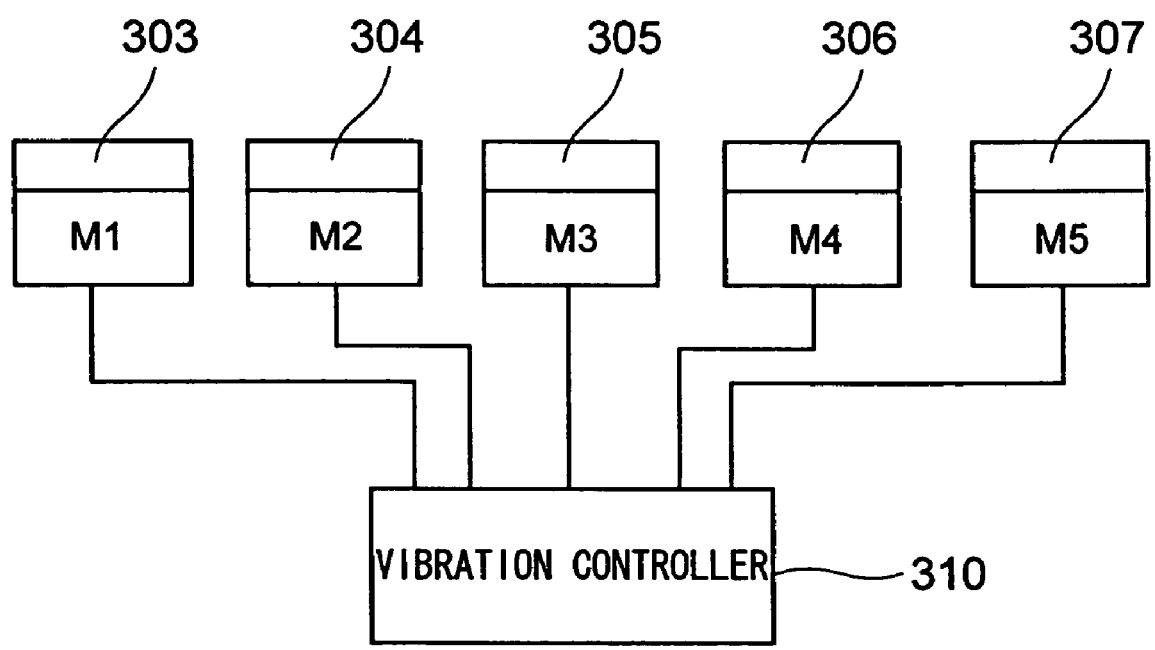
FIG. 7 is a block diagram showing the structure of a vibration section shown in FIG. 1.
Figure 8:
FIG. 8 is a schematic diagram showing an example of vibration pattern data stored in a database section.
Figure 8:
Figure 8:
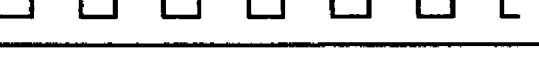
Figure 8:
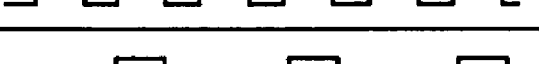
Figure 8:
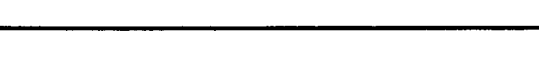
Figure 9:
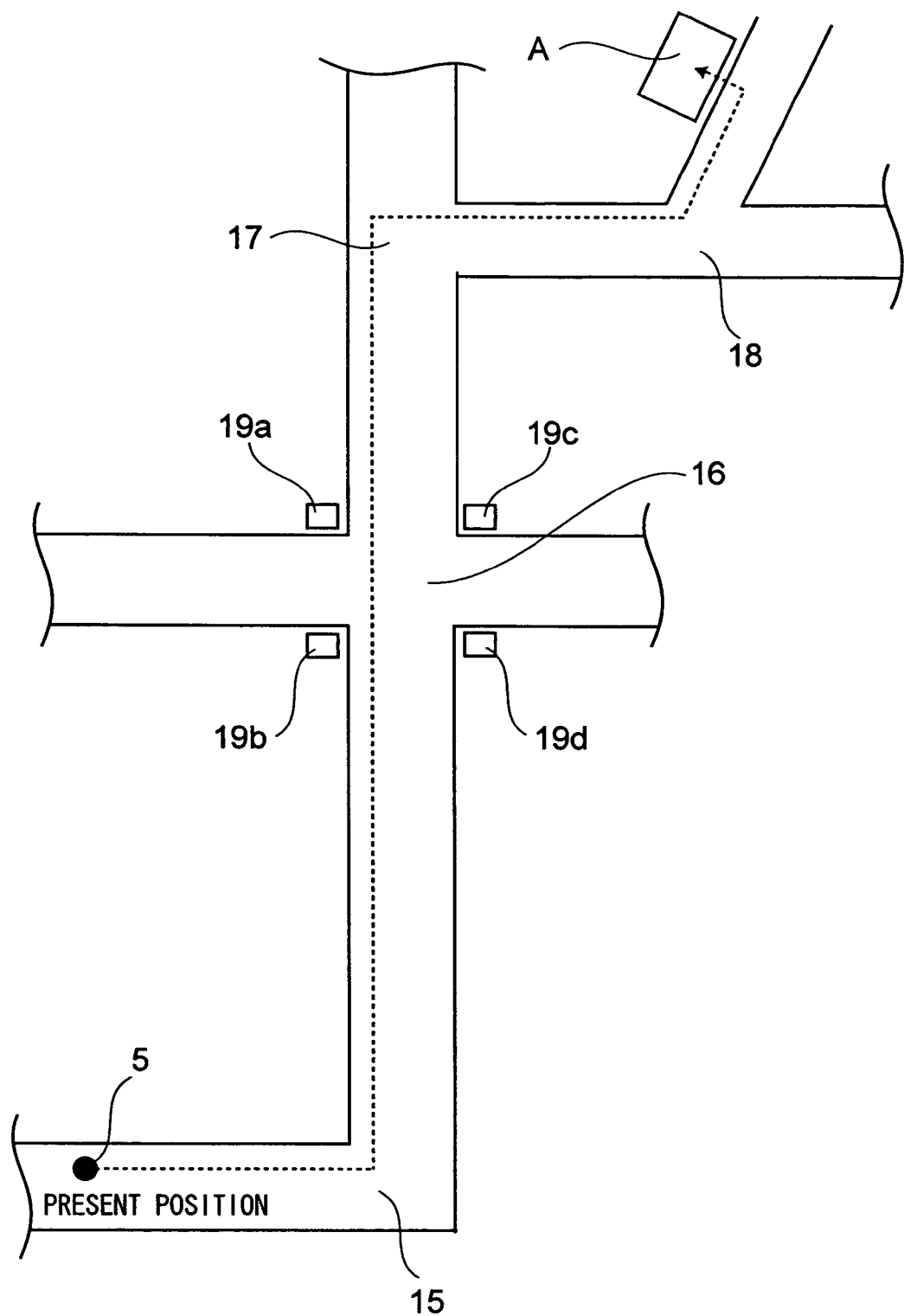
FIG. 9 is a schematic diagram showing a part of map information.
Figure 10:
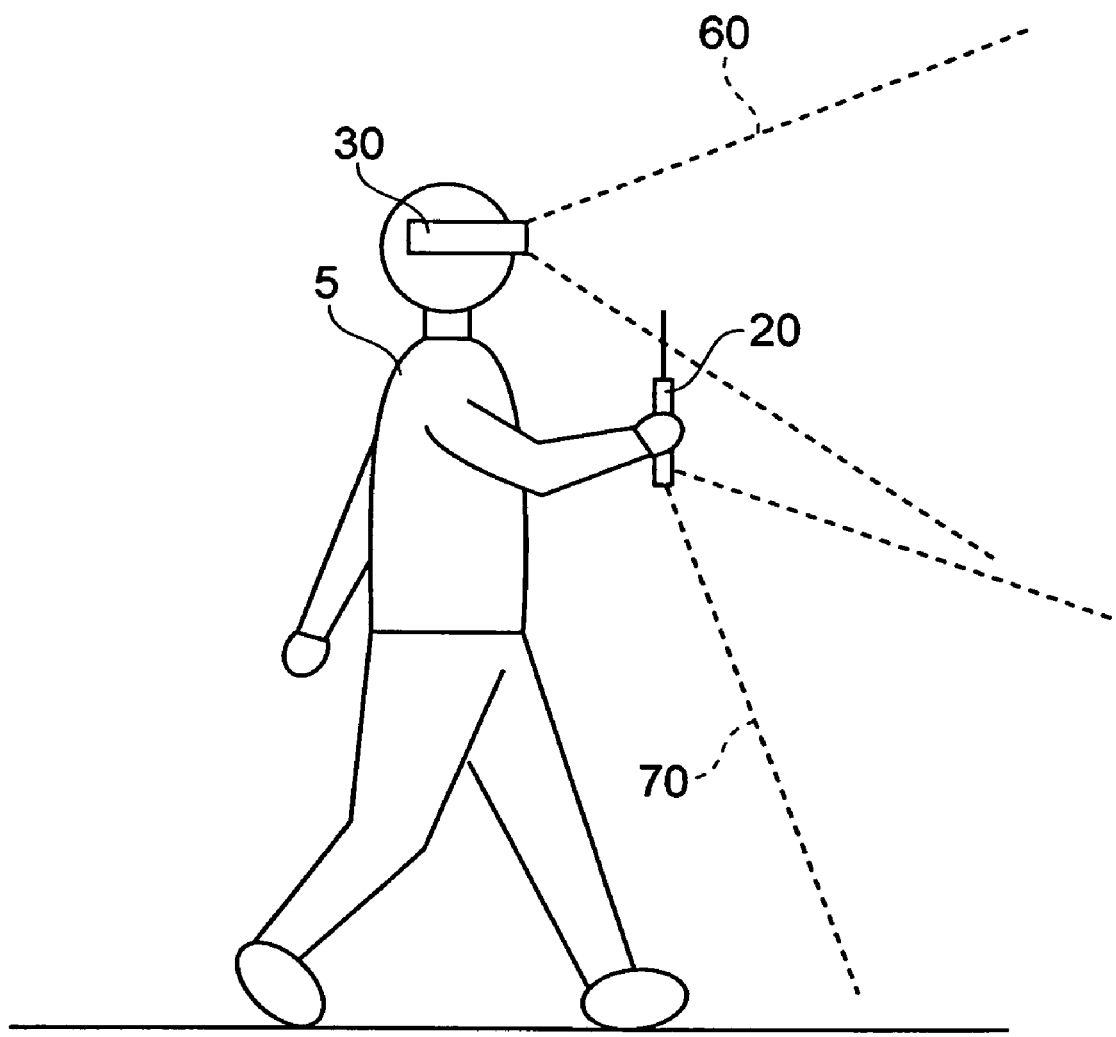
FIG. 10 is a schematic diagram showing the state that the user who puts on the information processing apparatus is walking.
Figure 11:
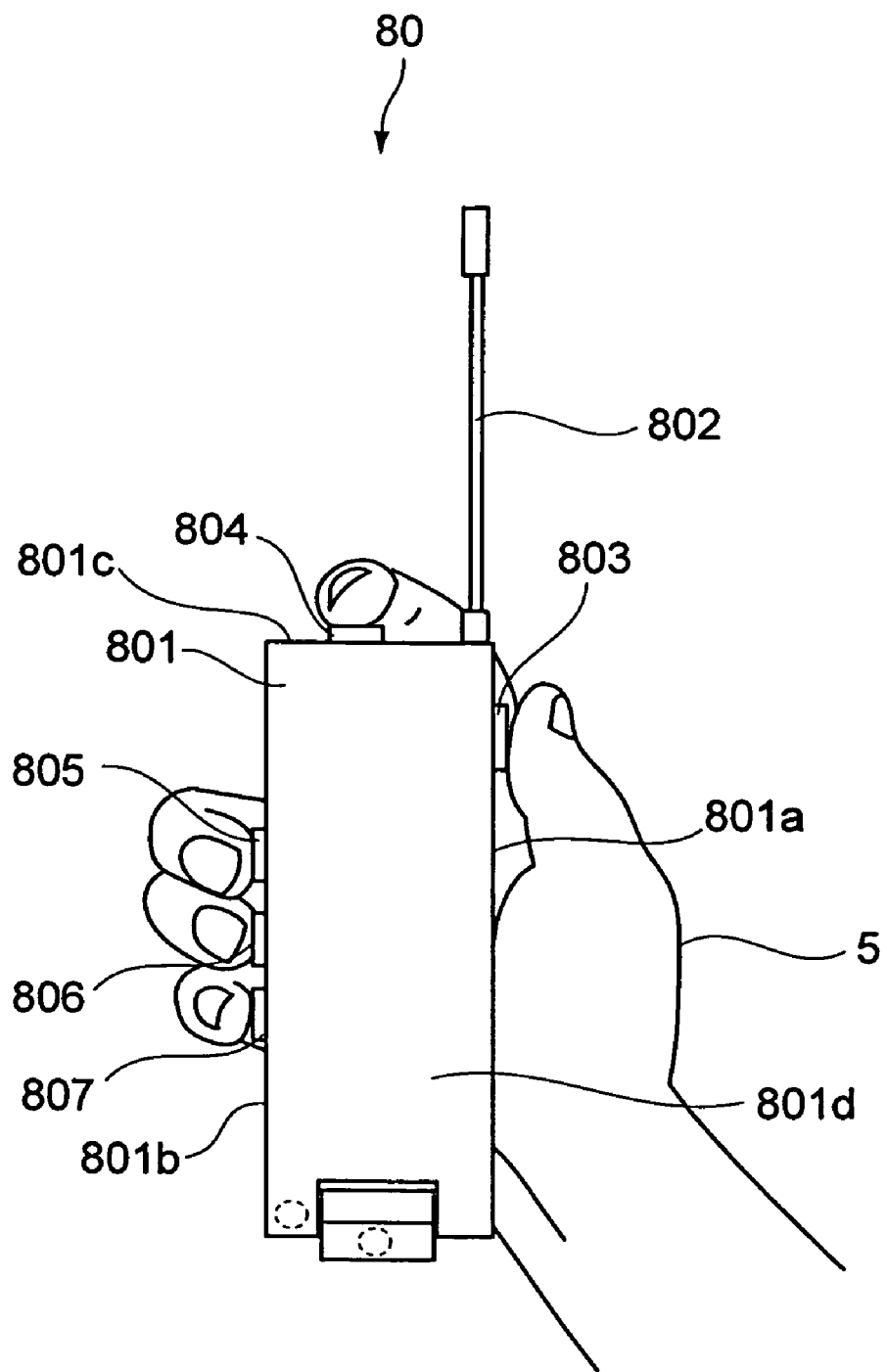
FIG. 11 is a perspective view showing a portable device according to another embodiment of the present invention.
Figure 12:
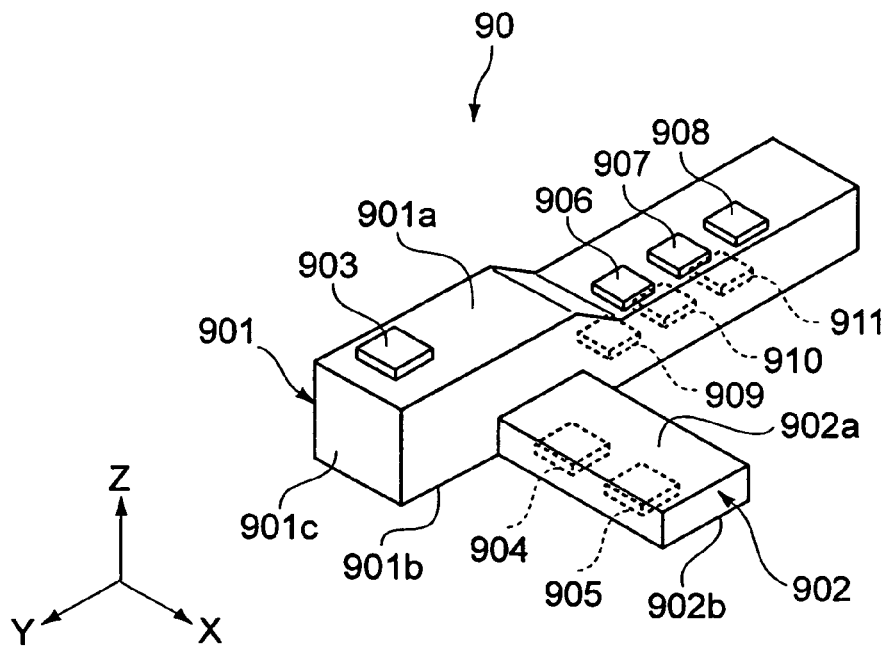
FIG. 12 is a perspective view showing a portable device according to a further other embodiment of the present invention.
Figure 13:
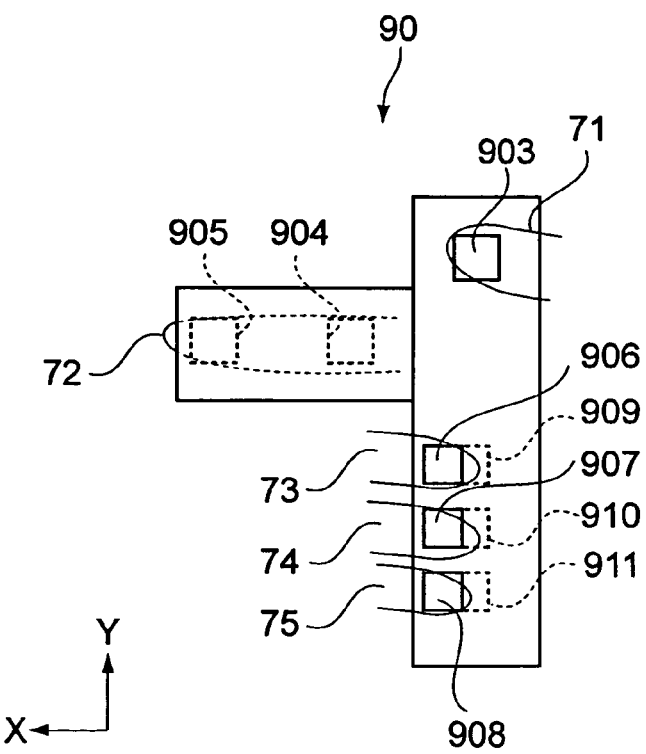
FIG. 13 is a plan view showing the portable device shown in FIG. 12.
Figure 14:
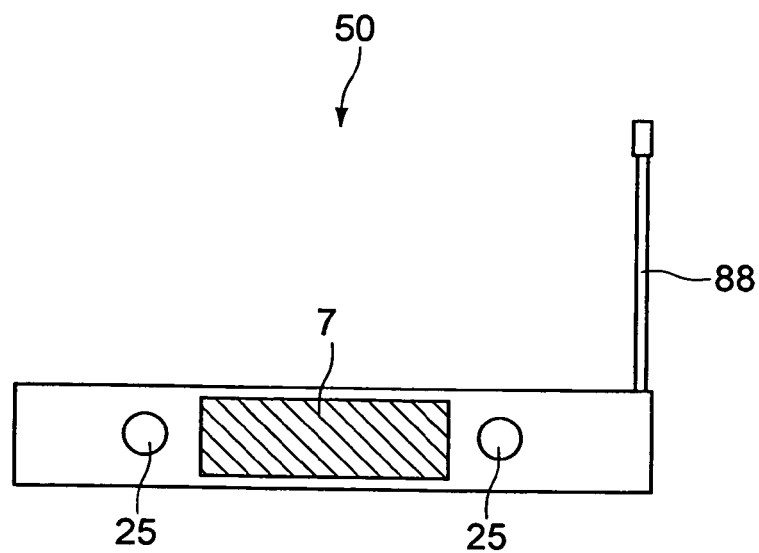
FIG. 14 is a plan view showing a mount device according to another embodiment of the present invention.
Figure 15:
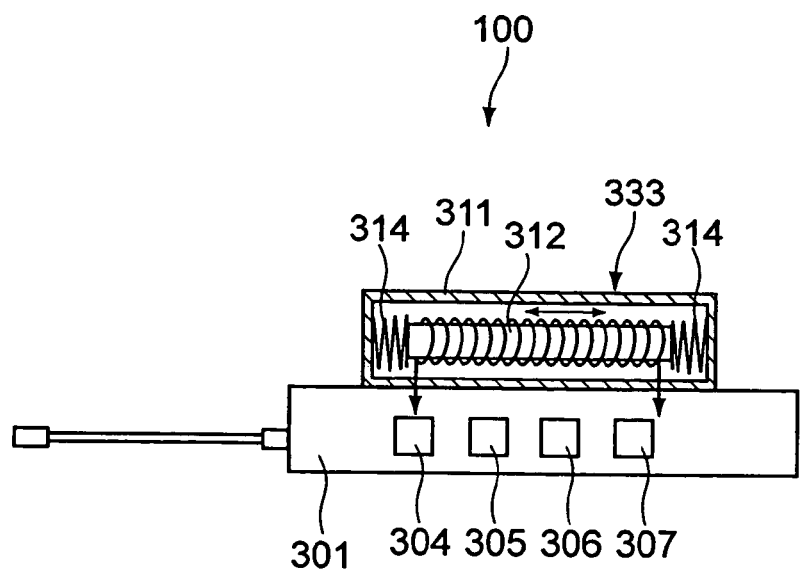
FIG. 15 is a side view showing a portable device according to the further other embodiment of the present invention.

1 Information Processing Apparatus
5 User
7 Solar Panel
11 Map Data
20, 50 mount device
21, 31 CPU
24 Speaker
25 Camera
26 Microphone
27 Communication Section
30, 80, 90, 100 Portable Device
35 Communication Section
36 Database Section
37 Camera
38 Vibration Section
39 Ultrasonic Sensor
40 Navigation Program
88 Antenna (Identification element)
301a First Side Surface
302a Second Side Surface
303~307, 803~807, 903~911 vibration Buttons
310 Vibration Controller
333 Power Generation Section

What is claimed is:

1. An information processing apparatus, comprising:
a mount device that is capable of being mounted to the user's head and that is capable of acquiring first picture information from information of user's surroundings; and
a portable device having:
means for storing map information,
means for acquiring user's any position information and second picture information of the user's surroundings, the second picture information being different from the first picture information,
means for setting a user's destination,
means for searching the map information for the destination that has been set and setting a route to the destination according to user's present position information, and
first informing means for informing the user of at least route information that has been set of the route information, the user's first picture information on the route and the user's second picture information on the route with vibration,
wherein the portable device has a main body that has a first surface and a second surface opposite to the first surface,
wherein the first informing means has a plurality of vibration buttons that vibrate user s fingers,
wherein each of the vibration buttons is composed of a first vibration button and a second vibration button disposed on the first surface and the second surface of the main body, respectively, and
wherein the first informing means has means for informing the user of the first picture information and the second picture information through the first vibration button and the second vibration button, respectively.

2. The information processing apparatus as set forth in claim 1,
wherein the mount device has:
second informing means for informing the user of at least one of the route information, the first picture information, and the second picture information with sound.

3. The information processing apparatus as set forth in claim 2,
wherein the portable device also has:
a sensor that detects an obstacle, and
wherein the first informing means or the second informing means has:
means for informing the user of information of the obstacle according to a detection signal of the sensor.

4. The information processing apparatus as set forth in claim 1,
wherein the first informing means has:
means for informing the user of a right-turn instruction and a left-turn instruction as the route information through the first vibration button and the second vibration button, respectively.

5. An information processing apparatus, comprising:
a mount device that is capable of being mounted to the user's head and that is capable of acquiring first picture information from information of user's surroundings; and a portable device having:
means for storing map information,
means for acquiring user's any position information and second picture information of the user's surroundings, the second picture information being different from the first picture information,
means for setting a user's destination, means for searching the map information for the destination that has been set and setting a route to the destination according to user's present position information, and first informing means for informing the user of at least route information that has been set of the route information, the user's first picture information on the route and the user's second picture information on the route with vibration, wherein the portable device has a main body that has a first surface and a second surface opposite to the first surface, wherein the first informing means has a plurality of vibration buttons that vibrate user's fingers, and means for varying the state of the vibration according to at least one of the route information, the first picture information, and the second picture information, and wherein each of the vibration buttons is composed of a first vibration button and a second vibration button disposed on the first surface and the second surface of the main body, respectively.

6. An information processing apparatus, comprising:

a mount device that is capable of being mounted to the user's head and that is capable of acquiring first picture information from information of user's surroundings; and a portable device having:

means for storing map information, means for acquiring user's any position information and second picture information of the user's surroundings, the second picture information being different from the first picture information, means for setting a user's destination, means for searching the map information for the destination that has been set and setting a route to the destination according to user's present position information, and first informing means for informing the user of at least route information that has been set of the route information, the user's first picture information on the route and the user's second picture information on the route with vibration, wherein the portable device has a main body that has a first surface and a second surface opposite to the first surface, wherein the first informing means has a plurality of vibration buttons that vibrate user s fingers, and means for outputting information in combination of vibration states of the vibration buttons, wherein each of the vibration buttons is composed of a first vibration button and a second vibration button disposed on the first surface and the second surface of the main body, respectively.

7. An information processing apparatus, comprising:

a mount device that is capable of being mounted to the user's head and that is capable of acquiring first picture information from information of user's surroundings; and a portable device having:

means for storing map information, means for acquiring user's any position information and second picture information of the user's surroundings, the second picture information being different from the first picture information, means for setting a user's destination, means for searching the map information for the destination that has been set and setting a route to the destination according to user's present position information, and first informing means for informing the user of at least route information that has been set of the route information, the user's first picture information on the route and the user's second picture information on the route with vibration, wherein the portable device has a main body that has a first surface and a second surface opposite to the first surface, means for storing position information of a predetermined facility as the map information, and means for informing the facility of the user's physiological state according to a user's operation input, wherein the route setting means has means for setting a route from the user's present position to the informed facility according to a user's operation input signal, wherein the first informing means has a plurality of vibration buttons that vibrate user s fingers, and wherein each of the vibration buttons is composed of a first vibration button and a second vibration button disposed on the first surface and the second surface of the main body, respectively.

8. A portable device, comprising:

a main body that has a first surface and a second surface opposite to the first surface; means for storing map information;

means for acquiring user's any position information and second picture information different from first picture information acquired by a mount device from information of user's surroundings, the mount device being capable of being mounted to the user's head;

means for setting a user's destination;

means for searching the map information for the destination that has been set and setting a route to the destination according to the user's present position information; and a first vibration button and a second vibration button that are disposed on the first surface and the second surface of the main body, that vibrate user's fingers so as to inform route information that has been set, and that vibrate user's'fingers so as to inform the user's first picture information on the route and the user's second picture information on the route, respectively.

9. An information processing method, comprising:

storing map information;

causing a mount device capable of being mounted to the user's head to acquire first picture information from information of user's surroundings;

acquiring user's present position information as map information;

setting a user's destination;

searching the map information for the destination that has been set;

setting a route to the destination according to the user's present position information;

causing a portable device that the user is capable of carrying and that has a main body having a first surface and a second surface opposite thereto and first vibration button and a second vibration button disposed on the first surface and the second surface, respectively, to acquire second picture information from the information of the user's surroundings, the second picture information being different from the first picture information; and informing the user of at least route information that has been set with vibration of the first vibration button and the second vibration button of the portable device, and informing the user of the user's first picture information on the route and the user's second picture information on the route through the first vibration button and the second vibration button, respectively.

10. A portable device, comprising:
a main body that has a first surface and a second surface opposite to the first surface;
means for storing map information;
means for acquiring user's any position information and second picture information different from first picture information acquired by a mount device from information of user's surroundings, the mount device being capable of being mounted to the user's head;
means for setting a user's destination;
means for searching the map information for the destination that has been set and setting a route to the destination according to the user's present position information; and
a first vibration button and a second vibration button that are disposed on the first surface and the second surface of the main body, that vibrate user's fingers so as to inform the user of at least route information that has been set of the route information, the user's first picture information on the route and the user's second picture information on the route with vibration, and that vary the state of the vibration according to at least one of the route information, the first picture information, and the second picture information.

11. An information processing method, comprising:
storing map information;
causing a mount device capable of being mounted to the user's head to acquire first picture information from information of user's surroundings;
acquiring user's present position information as map information;
setting a user's destination;
searching the map information for the destination that has been set;
setting a route to the destination according to the user's present position information;
causing a portable device that the user is capable of carrying and that has a main body having a first surface and a second surface opposite thereto and first vibration button and a second vibration button disposed on the first surface and the second surface, respectively, to acquire second picture information from the information of the user's surroundings, the second picture information being different from the first picture information; and
informing the user of at least route information that has been set of the route information, the first picture information on the route and the second picture information on the route with vibration of the first vibration button and the second vibration button of the portable device, and
varying the state of the vibration according to at least one of the route information, the first picture information, and the second picture information.

* * * * *